(12) United States Patent  
Chau et al.

(10) Patent No.: US 8,992,446 B2
(45) Date of Patent: Mar. 31, 2015

(54) PROCEDURE FOR DENOISING DUAL-AXIS SWALLOWING ACCELEROMETRY SIGNALS

(75) Inventors: Tom Chau, Toronto (CA); Ervin Sejdic, Toronto (CA)

(73) Assignee: Holland Bloorview Kids Rehabilitation Hospital, Toronto (CA)

( * ) Notice: Subject to any disclaimer, the term of this patent is extended or adjusted under 35 U.S.C. 154(b) by 348 days.

(21) Appl. No.: 12/819,216

(22) Filed: Jun. 20, 2010

(65) Prior Publication Data

US 2012/0271872 A1 Oct. 25, 2012

Related U.S. Application Data

(60) Provisional application No. 61/218,976, filed on Jun. 21, 2009.

(51) Int. Cl.
*A61B 5/103* (2006.01)
*G06F 17/18* (2006.01)
*A61B 5/00* (2006.01)

(52) U.S. Cl.
CPC .............. *G06F 17/18* (2013.01); *A61B 5/4205* (2013.01); *A61B 5/7203* (2013.01); *A61B 5/726* (2013.01)
USPC ........... 600/593; 600/595; 708/200; 708/309; 708/811; 703/5

(58) Field of Classification Search
CPC ................................ G06F 17/30; G06F 17/00
See application file for complete search history.

(56) References Cited

U.S. PATENT DOCUMENTS 3,683,378 A * 8/1972 Polhemus ...................... 342/107
3,805,032 A * 4/1974 Ross ............................. 702/181

(Continued)

FOREIGN PATENT DOCUMENTS

EP 1773184 A1 4/2007
WO 0226101 4/2002

(Continued)

OTHER PUBLICATIONS

Lee, J., Steele, C.M., and Chau, T., "Time and time-frequency characterization of dual-axis swallowing accelerometry signals," Aug. 28, 2008, IOP Publishing—Physiological Measurement, issue 29, pp. 1105-1120.*

(Continued)

*Primary Examiner* — Farhan Syed
(74) *Attorney, Agent, or Firm* — K&L Gates LLP

(57) ABSTRACT

Dual-axis swallowing accelerometry is an emerging tool for the assessment of dysphagia (swallowing difficulties). These signals however can be very noisy as a result of physiological and motion artifacts. A novel scheme for denoising those signals is proposed, i.e., a computationally efficient search for the optimal denoising threshold within a reduced wavelet subspace. To determine a viable subspace, the algorithm relies on the minimum value of the estimated upper bound for the reconstruction error. A numerical analysis of the proposed scheme using synthetic test signals demonstrated that the proposed scheme is computationally more efficient than minimum noiseless description length (MNDL) based denoising. It also yields smaller reconstruction errors (i.e., higher signal-to-noise (SNR) ratio) than MNDL, SURE and Donoho denoising methods. When applied to dual-axis swallowing accelerometry signals, the proposed scheme improves the SNR values for dry, wet and wet chin tuck swallows. These results are important to the further development of medical devices based on dual-axis swallowing accelerometry signals.

7 Claims, 3 Drawing Sheets

(56) References Cited

U.S. PATENT DOCUMENTS

| | | | |
|---|---|---|---|
| 4,910,398 A * | 3/1990 | Komatsu et al. | 250/307 |
| 5,024,240 A | 6/1991 | McConnel | |
| 5,143,087 A | 9/1992 | Yarkony | |
| 5,263,491 A * | 11/1993 | Thornton | 600/587 |
| 5,274,548 A * | 12/1993 | Bernard et al. | 600/500 |
| 5,353,223 A * | 10/1994 | Norton et al. | 702/17 |
| 5,363,858 A | 11/1994 | Farwell | |
| 5,442,562 A * | 8/1995 | Hopkins et al. | 700/108 |
| 5,445,144 A | 8/1995 | Wodicka et al. | |
| 5,497,777 A * | 3/1996 | Abdel-Malek et al. | 600/443 |
| 5,505,410 A * | 4/1996 | Diesel et al. | 244/195 |
| 5,610,609 A * | 3/1997 | Rose | 342/13 |
| 5,619,998 A * | 4/1997 | Abdel-Malek et al. | 600/437 |
| 5,625,704 A * | 4/1997 | Prasad | 382/118 |
| 5,704,017 A * | 12/1997 | Heckerman et al. | 706/12 |
| 5,704,018 A * | 12/1997 | Heckerman et al. | 706/12 |
| 5,729,700 A * | 3/1998 | Melnikoff | 705/36 R |
| 5,737,487 A * | 4/1998 | Bellegarda et al. | 704/250 |
| 5,745,654 A * | 4/1998 | Titan | 706/20 |
| 5,784,696 A * | 7/1998 | Melnikoff | 705/36 R |
| 5,802,256 A * | 9/1998 | Heckerman et al. | 706/59 |
| 5,891,185 A | 4/1999 | Freed et al. | |
| 5,909,189 A * | 6/1999 | Blackman et al. | 342/90 |
| 5,970,978 A | 10/1999 | Aviv et al. | |
| 6,028,841 A * | 2/2000 | Lyon et al. | 370/232 |
| 6,033,073 A * | 3/2000 | Potapova et al. | 351/211 |
| 6,036,349 A * | 3/2000 | Gombar | 703/6 |
| 6,061,631 A * | 5/2000 | Zhang | 701/470 |
| 6,157,912 A * | 12/2000 | Kneser et al. | 704/270 |
| 6,267,729 B1 | 7/2001 | Addington et al. | |
| 6,272,377 B1 * | 8/2001 | Sweeney et al. | 600/515 |
| 6,383,142 B1 | 5/2002 | Gavriely | |
| 6,443,895 B1 * | 9/2002 | Adam et al. | 600/443 |
| 6,445,942 B1 | 9/2002 | Berthon-Jones et al. | |
| 6,463,328 B1 | 10/2002 | John | |
| 6,568,397 B1 | 5/2003 | Addington et al. | |
| 6,581,605 B2 | 6/2003 | Addington et al. | |
| 6,620,100 B2 | 9/2003 | Smits et al. | |
| 6,745,184 B1 * | 6/2004 | Choi et al. | 1/1 |
| 6,826,513 B1 * | 11/2004 | Kumar et al. | 702/185 |
| 6,928,434 B1 * | 8/2005 | Choi et al. | 1/1 |
| 6,978,787 B1 | 12/2005 | Broniatowski | |
| 6,987,511 B2 * | 1/2006 | Taubin | 345/420 |
| 7,253,627 B1 | 8/2007 | Ahmed | 324/322 |
| 7,398,270 B1 * | 7/2008 | Choi et al. | 1/1 |
| 7,421,377 B2 * | 9/2008 | Zhang | 702/191 |
| 7,526,402 B2 * | 4/2009 | Tanenhaus et al. | 702/151 |
| 7,672,717 B1 * | 3/2010 | Zikov et al. | 600/544 |
| 7,721,961 B2 | 5/2010 | Silverbrook et al. | |
| 7,930,145 B2 * | 4/2011 | Hel-Or et al. | 702/189 |
| 8,041,136 B2 * | 10/2011 | Causevic | 382/249 |
| 8,239,162 B2 * | 8/2012 | Tanenhaus | 702/151 |
| 8,267,875 B2 | 9/2012 | Chau et al. | |
| 2002/0133194 A1 | 9/2002 | Leelamanit et al. | |
| 2003/0018276 A1 | 1/2003 | Mansy et al. | |
| 2003/0073920 A1 | 4/2003 | Smits et al. | |
| 2004/0075659 A1 * | 4/2004 | Taubin | 345/428 |
| 2004/0147816 A1 | 7/2004 | Policker et al. | |
| 2004/0260169 A1 * | 12/2004 | Sternnickel | 600/409 |
| 2005/0283096 A1 * | 12/2005 | Chau et al. | 600/593 |
| 2005/0286772 A1 | 12/2005 | Albertelli | |
| 2006/0064037 A1 | 3/2006 | Shalon et al. | |
| 2006/0074823 A1 | 4/2006 | Heumann et al. | |
| 2006/0120609 A1 | 6/2006 | Ivanov et al. | |
| 2007/0032951 A1 * | 2/2007 | Tanenhaus et al. | 701/220 |
| 2007/0238920 A1 * | 10/2007 | Sato et al. | 600/102 |
| 2008/0103717 A1 * | 5/2008 | Hel-Or et al. | 702/107 |
| 2008/0146890 A1 | 6/2008 | LeBoeuf et al. | |
| 2008/0243017 A1 * | 10/2008 | Moussavi et al. | 600/532 |
| 2008/0262371 A1 * | 10/2008 | Causevic | 600/544 |
| 2008/0269646 A1 * | 10/2008 | Chau et al. | 600/595 |
| 2008/0306373 A1 * | 12/2008 | Kandori et al. | 600/407 |
| 2009/0030346 A1 * | 1/2009 | Kojima et al. | 600/590 |
| 2009/0198306 A1 * | 8/2009 | Goetz et al. | 607/59 |
| 2009/0263034 A1 * | 10/2009 | Causevic | 382/249 |
| 2009/0264786 A1 * | 10/2009 | Jacquin | 600/544 |
| 2009/0326851 A1 * | 12/2009 | Tanenhaus | 702/96 |
| 2010/0160833 A1 * | 6/2010 | Chau et al. | 600/593 |
| 2010/0161238 A1 * | 6/2010 | Cappadona et al. | 702/19 |
| 2010/0217089 A1 | 8/2010 | Farley et al. | |
| 2010/0217099 A1 | 8/2010 | LeBoeuf et al. | |
| 2010/0250173 A1 | 9/2010 | Kozu | |
| 2010/0250473 A1 | 9/2010 | Porikli et al. | |
| 2010/0306144 A1 | 12/2010 | Scholz et al. | |
| 2011/0170796 A1 * | 7/2011 | Qian et al. | 382/264 |
| 2012/0271872 A1 * | 10/2012 | Chau et al. | 708/309 |
| 2013/0184538 A1 * | 7/2013 | Lee et al. | 600/301 |

FOREIGN PATENT DOCUMENTS

| | | |
|---|---|---|
| WO | 02082968 | 10/2002 |
| WO | 2004011035 | 2/2004 |
| WO | 2005023105 A1 | 3/2005 |

OTHER PUBLICATIONS

"A radial basis classifier for the automatic detection of aspiration in children with dysphagia," by Tom Chau et al., Journal of Neuroengineering and Rehabilitation, 2006, vol. 3, issue 14, pp. 1-11.*

Lee, Joonwu, "Investigation of Accelerometry, Mechanomyography, and Nasal Airflow Signals for Abnormal Swallow Detection," 2009, University of Toronto, Department of Electrical and Computer Engineering, pp. i-188 (204 total pages).*

Raya, Mary Anne D., et al, "Adaptive Noise Cancelling of Motion Artifact in Stress ECG Signals Using Accelerometer," IEEE, Proceedings of the Second Joint EMBS/BMES Conference, Oct. 23-26, 2002, pp. 1756-1757 (2 total pages).*

Beheshti, Soosan, et al., "A New Information-Theoretic Approach to Signal Denoising and Best Basis Selection," Oct. 2005, IEEE Transactions on Signal Processing, vol. 53, No. 10., pp. 3613-3624 (12 total pages).*

Chau, Tom, et al., "A procedure for denoising dual-axis swalling accelerometry signals," Nov. 26, 2009, Physiological Measurement, Issue 31, pp. N1-N9 (9 total pages).*

Chang, S. Grace, et al., "Adaptive Wavelet Thresholding for Image Denoising and Compression," Sep. 2000, IEEE Transactions on Image Processing, vol. 9, No. 9, pp. 1532-1546 (15 total pages).*

Chau, Tom, et al., "Investigating the Stationarity of Paediatric Aspiration Signals," Mar. 2005, IEEE Transactions on Nueral Systems and Rehabilitation Engineering, vol. 13, No. 1, pp. 99-105 (7 total pages).*

D65. J. Lee, C. M. Steele, and T. Chau, "Swallow segmentation with artificial neural networks and multi-sensor fusion," Medical Engineering and Physics, vol. 31, No. 9, pp. 1049-1055. Nov. 2009.

D66. J. Lee, T. Chau and C. M. Steele. Effects of Age and Stimulus on Submental Mechanomyography Signals During Swallowing. Dysphagia, 24(3):265-273, 2009.

W24. J.A. Hind, G. Gensler, D.K. Brandt, P.J. Miller, Gardner, L. Blumenthal, G.D. Gramigna, S. Kosek D. Lundy, S. McGarvey-Toker, S. Rockafellow, et al. Comparison of trained clinician ratings with expert ratings of aspiration on videofluoroscopic images from a randomized clinical trial. Dysphagia, 24(2):211-217, 2009.

W9. Pauloski BR, Rademaker AW, Kern M, Shaker R, Logemann JA: The feasibility of establishing agreement between laboratories for measures of oropharyngeal structural movements. J Med Speech Lang Pa. 2009;17: 9-19.

W14. R. Martino, D. L. Stre, Iner E. Maki, and N. Diamant "A sensitivity analysis to determine whether ten teaspoons of water are really necessary," Dysphagia, vol. 24, No. 4, p. 473, Dec. 2009.

D67. R. Martino, F. Silver, R. Teashell, M. Bayley, G. Nicholson, D. L. Streiner, and N. E. Diamant, "The toronto bedside swallowing screening test (TOR-BSST): Development and validation of a dysphagia screening tool for patients with stroke," Stroke, vol. 40, No. 2, pp. 555-561, Feb. 2009.

D68. Singapore Ministry of Health. Stroke and transient ischaemic attacks: Assessment, investigation, immediate management and secondary prevention. Clinical practice guidelines. 2009. http://www.

(56) References Cited

OTHER PUBLICATIONS moh.gov.sg/mohcorp/uploadedFiles/Publications/Guidelines/Clinical_Practice_Guidelines/Stroke%20Booklet.pdf.

W16. Logemann Ja, Rademaker A, Pauloski Br, Kelly A, Strangl-McBreen C, Antinoka J, Grande B, Farquharson J, Kern M, Easterling C: A randomized study comparing the Shaker exercise with traditional therapy: a preliminary study. Dysphagia. 2009:24:403-411.

D69. C. M. Steele, T. Chau, G. Bailey, J. Bennett, N. B. N, R. Cliffe, S. M. Molfenter, M. Takeuchi, A. Waito, A. Weeda, and D. Zoratto, "Sensitivity and specificity of a standardized swallow screening protocol: Validation against concurrent videofluoroscopy," Dysphagia, vol. 25, No. 4, p. 359, Dec. 2010.

W1. C.S.S. Greco, L.G.M.Q. Nunes, P.L. Melo, "Instrumentation for Bedside Analysis of Swallowing Disorders," 32nd Annual International Conference of the IEEE EMBS, Buenos Aires, Argentina, Aug. 31-Sep. 4, 2010.

D70. Damouras, et al., "An Online Swallow Detection Algorithm . . . Dual-Axis Accelerometry," IEEE Transactions on Signal Processing, Jun. 2010, No. 6, pp. 3352-3359, vol. 58.

D71. E. Sejdic, C. M. Steele, and T. Chau, "A procedure for denoising dual-axis swallowing accelerometry signals," Physiological Measurement, vol. 31, No. 1, pp. N1-N9, Jan. 2010.

D72. E. Sejdic, M. Steele, and T. Chau, "Understanding the statistical persistence of dual-axis swallowing accelerometry signals," Computers in Biology and Medicine, vol. 40, No. 11-12, pp. 839-844, 2010.

D73. E. Sejdic, T. H. Falk, C. M. Steele, and T. Chau, "Vocalization removal for improved automatic segmentation of dual-axis swallowing accelerometry signals," Medical Engineering and Physics, vol. 32, No. 6, pp. 668-672, Jul. 2010.

D74. E. Sejdic, V. Komisar, C. M. Steele, and T. Chau, "Baseline characteristics of dual-axis cervical accelerometry signals," Annals of Biomedical Engineering, vol. 38, No. 3, pp. 1048-1059, Mar. 2010.

D75. Esteves, et al.,"Configurable Portable/Ambulatory Instrument for the Analysis of the Coordination between Respiration & Swallowing,"32nd Annual Inti Conf of IEEE, Sep. 2010.

D76. F. Hanna, S. Molfenter, R. Cliffe, T. Chau, and C. Steele, "Anthropometric and demographic correlates of dual-axis swallowing accelerometry signal characteristics: A canonical correlation analysis," Dysphagia, vol. 25, No. 2, pp. 94-103, Jun. 2010.

D77. Orovic, S. Stankovic, T. Chau, C. M. Steele, and E. Sejdic, "Time-frequency analysis and Hérmite projection method applied to swallowing accelerometry signals," EURASIP Journal on Advances in Signal Processing, vol. 2010, 2010, article ID 323125, 7 pages.

D78. Lee, E. Sejdic, C. Steele, and T. Chau, "Effects of liquid stimuli on dual-axis swallowing acceleromretry signals in a healthy population," BioMedical Engineering OnLine, vol. 9, pp. 7-1-7-14, 2010.

D79. Management of Patients with Stroke: Identification and Management of Dysphagia, Scottish Intercollegiate Guidelines Network, Edinburgh, Scotland, Jun, 2010.

D80. Sejdic et al., "The Effects of Head Movement on Dual-Axis Cervical Accelerometry Signals," BMC Research Notes, 2010, vol. 3.

D81. A. Waito, G. L. Bailey, S. M. Molfenter, D. C. Zoratto, and C. M. Steele, "Voice-quality abnormalities as a sign of dysphagia: Validation against acoustic and videofluoroscopic data," Dysphagia, vol. 26, No. 2, pp. 125-134, Jun. 2011.

D82. C. M. Steele, G. L. Bailey, T. Chau, S. M. Molfenter, M. Oshalla, A. A. Waito, and D. Zoratto, "The relationship between hyoid and laryngeal displacement and swallowing impairment," Clinical Otolaryngology, vol. 36, No. 1, pp. 30-36, Feb. 2011.

D83. E. Sejdic, C. M. Steele, and T. Chau, "Scaling analysis of baseline dual-axis cervical accelerometry signals," Computer Methods and Programs in Biomedicine, vol. 103, No. 3, pp. 113-120, Sep. 2011.

D84. Lee, C. M. Steele, and T. Chau, "Classification of healthy and abnormal swallows based on accelerometry and nasal airflow signals," Artificial Intelligence in Medicine, vol. 52, No. 1, pp. 17-25, May 2011.

W20. Leder, et al., "Silent Aspiration Risk is Volume-Dependent," Dysphagia, Sep. 2011, No. 3, pp. 304-309, vol. 26.

W12. Omari TI, Dejaeger E, Van Beckevoort D, Goeleven A, De Cock P, Hoffman I, Smet MH, Davidson GP, Tack J, Rommel N: A novel method for the nonradiological assessment of ineffective swallowing. Am J Gastroenterol. 2011;106: 1796-1802.

W4. Ryu JS, Lee JH, Kang JY, Kim MY, Shin DE, Shin DA: Evaluation of dysphagia after cervical surgery using laryngeal electromyopraphy. Dysphagia. 2011;epub ahead of print. DOI 10.1007/s00455-011-9368-7. 1-7.

D85. S.R.Youmans, J.A.G. Stierwalt, "Normal Swallowing Acoustics Across Age, Gender, Bolus, Viscosity, and Bolus Volume," Dysphagia (2011) 26:374-384.

D86. Steele. C.M. et al., Nonimasiye detection of thin-liquid aspiration using dual-axis swallowing accelerometry . . . Dysphagia. Jul. 28, 2012. pp. 105-112. url <http:/hww.ncbi.nlm.gm/pmc/articles/PMC3576558/pdf/-J.55_2012_Article_9-J.I8.pdf>.

D24. Das, Reddy and Narayanan, "Hybrid fuzzy logic committee neural networks for recognition of swallow acceleration signals", Computer Methods and Programs In Biomedicine, 64 (2001) 87-99, Elsevier Science Ireland Ltd.

D44. Chau, et al.,"Investigating the Stationarity of Paediatric Aspiration Signals, "Transactions on Neural Systems and Rehabilitation Engineering, Mar. 2005, No. 1, pp. 99-105, vol. 13.

D2. W. J. Dodds, K. M. Man, I. J.Cook, P. J. Kahrilas, E. T. Stewart, and M. K. Kern, "Influence of bolus volume on swallow-induced hyoid movement in normal subjects," American Journal of Roentgenology, vol. 150, No. 6, pp. 1307-1309, Jun. 1988.

D4. Lof, et al., "Test-Retest Variability in Normal Swallowing," Dysphagia, 1990, pp. 236-242, vol. 4.

W7. Perlman AL, Grayhack JP, Booth BM: The relationship of vallecular residue to oral involvement, reduced hyoid elevation, and epiglottic function. J Speech Hear Res. 1992;35:734-174.

D12. Perlman LP, Vandaele DJ, Otterbacher MS; Quantitative Assessment of Hyoid Bone Displacement from Video Images During Swallowing; Journal of Speech and Hearing Research, vol. 38, 579-585, Jun. 1995.

D14. J. C. Rosenbek, J. A. Robbins, E. B. Roecker, J. L.Coyle, and J. L. Wood, "A penetration-aspiration scale," Dysphagia, vol. 11, No. 2, pp. 93-98, Mar. 1996.

W5. Rosenbek JC, Roecker EB, Wood JL, Robbins JA: Thermal application reduces the duration of stage transition in dysphagia after stroke. Dysphagia, 1996;11:225-233.

W30. Dejaeger E, Pelemans W, Ponette E, Joosten E: Mechanisms involved in postdeglutition retention in the elderly. Dysphagia. 1997;12:63-67.

W23. Kahrilas PJ, Lin S, Rademaker AW, Logemann JA; Impaired Deglutitive Airway Protection: A Videofluoroscipic Analysis of Severity and Mechanism; Gastroenterology 1997; 113:1457-1464.

W22. Kuhlemeier KV, Yates P, Palmer JB: Intra-and interrater variation in the evaluation of videofluorographic swallowing studies. Dysphagia. 1998;13:142-147.

W11. Sellars, Dunnet and Carter, "A Preliminary Comparison of Videofluoroscopy of Swallow and Pulse Oximetry In the Identification of Aspiration in Dysphagic Patients", Dysphagia, 13:82-86 (1998), Springer-Verlag New York Inc.

D20. A. S. Halper, L. R. Cherney, K. Cichowski, and M. Zhang, "Dysphagia after head trauma: The effect of cognitive-communicative impairments on functional outcomes," Journal of Head Trauma Rehabilitation, vol. 14, No. 5, pp. 486-496, Oct. 1999.

D21. Zoratto, et al., "Hyolaryngeal Excursion as the Physiological Source of Swallowing Accelerometry Signals," D Physiological Measurement, 2010, pp. 844-855, vol. 31. Diagnosis and Treatment of Swallowing Discorders (Dysphagia) in Acute-Care Stroke Patients, Agency for D Healthcare Research and Quality, Mar. 1999.

W17. Logemann JA, Pauloski BR, Rademaker AW, Colangelo LA, Kahrilas PJ, Smith CH; Temporal and Biomechanical Characteristics

(56) References Cited

OTHER PUBLICATIONS of Oropharyngeal swallow in Younger and Older Men; Journal of Speech, Language, and Hearing Research: Oct. 2000; 46, 5; Research Library p. 1264.

D23. Reddy, Katakam, Gupta, Unnikrishnan, Narayanan and Canilang, "Measurement of acceleration during 1 videofluorographic evaluation of of dysphagic patients", Medical Engineering & Physics; 22 (2000) 405-412, Elsevier D Science Ireland Ltd.

W26. Han TR, Paik NJ, Park JW: Quantifying swallowing function after stroke: A functional dysphagia scale based on videofluoroscopic studies. Arch Phys Med Rehabil. 2001;82:677-682.

W25. Hind JA, Nicosia MA, Roecker EB, Carnes ML, Robbins JA: Comparison of effortful and noneffortful swallows in healthy middle-aged and older adults. Arch Phys Med Rehabil. 2001;82:1661-1665.

D25. L. Perry, "Screening swallowing function of patients with acute stroke. part two: detailed evaluation of the tool used by nurses," Journal of Clinical Nursing, vol. 10, No. 4, pp. 474-481, Jul. 2001.

D26. McCullough GH, Wertz RT, Rosenbek JC, Mills RH, Webb WG, Ross KB: Inter-and intrajudge reliability for videofluoroscopic swallowing evaluation measures. Dysphagia. 2001;16:110-118.

D29. Chau, Casas, Berall and Kenny, Poster Presentation; "To characterize normality and stationarity properties of pediatric aspiration signals", Houston, Texas, Oct. 2002.

D31. Cichero and Murdoch, "Detection of Swallowing Sounds: Methodology Revisited", Dysphagia, 17:40-49 (2002), Springer-Veriag New York Inc.

D32. Cichero, et al., "Acoustic Signature of the Normal Swallow: Characterization by Age, Gender, and Bolus Volume, " The Annals of Otology, Rhinology & Laryngology, Jul. 2002, No. 7, pp. 623-632, val. 111.

W27. Eisenhuber E, Schima W, Schober E, Pokieser P, Stadler A, Scharitzer M, Oschatz E: Videofluoroscopic assessment of patients with dysphagia: Pharyngeal retention is a predictive factor for aspiration. Am J Roentgenol. 2002; 178:393-398.

D33. Ishida R, Palmer JB, Hiiemae KM: Hyoid Motion During Swallowing: Factors Affecting Forward and Upward Displacement. Dysphagia. 2002;17:262-272.

W18. Logemann JA, Pauloski BR, Rademaker AW, Kahrilas PJ; Oropharyngeal Swallow in Younger and Older Women: Videofluoroscopic Analysis; Journal of Speech, Language, and Hearing Research: Jun. 2002; 45, 3; Research Library p. 434.

W8. Pauloski BR, Rademaker AW, Logemann JA, Lazarus CL, Newman L, Hamner A, Maccraken E, Gaziano J, Staceiowiak L: Swallow function and perception of dysphagia in patients with head and neck cancer. Head Neck. 2002;24:555-565.

D36. Cichero, et al., "What Happens After the Swallow" Introducing the Glottal Release Sound, Journal of Medical Speech—Language Pathology, Mar. 2003, No. 1, pp, 31-41, vol. 11.

D40. Stoeckli et al.: Interraterreliability of videofluoroscopic swallow evaluation. Dysphagia. 2003;18:53-57.

W2. Suiter DM, McCullogh GH, Powell PW: Effects of cuff deflation and one-way tracheostomy speaking valve placement on swallow physiology. Dysphania. 2003;18:284-292.

D41. Joint Commission. Stroke performance measurement implementation guide. 2004. http://www.jointcommission.org/CertificationPrograms/Disease-SpecificCare/Standards/09_FAQs+_PrimaryStrokeCenter/PerfM/For+which+patients.htm.

W3. C. M. Steele and P. H. H. M. Van Lieshout, "Influence of bolus consistency on lingual behaviors in sequential swallowing," Dysphagia, vol. 19, No. 3. pp. 192-206, Aug. 2004.

W19. Logemann JA, Williams RB, Rademaker A, Pauloski BR, Lazarus CL, Cook I: The relationship between observations and measures of oral and pharyngeal residue from videofluorography and scintigraphy. Dysphagia. 2005;20:226-231.

W13. R. Martino, N. Foley, S. Bhogal, N. Diamant, M. Speechley, and R. Teasell, "Dysphagia after stroke: Incidence, diagnosis, and pulmonary complications," Stroke, vol. 36, No. 12, pp. 2756-2763, Dec. 2005.

W29. A. Daggett, J. Logemann, A. Rademaker, and B. Pauloski, "Laryngeal penetration during deglutition in normal subjects of various ages," Dysphagia, vol. 21, No. 4, pp. 270-274, Oct. 2006.

W32. Clavé P, De Kraa M, Arreola V, Girvent M, Farré R, Palomera E, Serra-Prat M: The effect of bolus viscosity on swallowing function in neurogenic dysphagia. Aliment Pharmacol Ther. 2006;24:1385-1394.

D49. C. Borr, M. Hielscher-Fastabend, and A. Lucking. Reliability and validity of cervical auscultation. Dysphagia, 22(3):225-234, Jul. 2007. LR: 20071115; JID: 8610856; Mar. 23, 2006 [received]; Jan. 18, 2007 [accepted]; Apr. 25, 2007 [a head of print]; publish.

W6. Robbins JA, Kays SA, Gangnon RE, Hind JA, Hewitt AL, Gentry LR, Taylor AJ: The effects of lingual exercise in stroke patients with dysphagia. Arch Phys Med Rehabil. 2007;88:150-158.

W15. B. Martin-Harris, M. Brodsky, Y. Michel, D. Castell, M. Schleicher, J. Sandidge, R. Maxwell, and J. Blair, "MBS measurement tool for swallow impairment—MBSImp: Establishing a standard," Dysphagia, vol. 23, No. 4, pp. 392-405, Dec. 2008.

D53. Clave, et al., "Accuracy of the volume-viscosity swallow test for clinical screening of oropharyngeal dysphagia . . . ," Clinical Nutrition, Dec. 2008, No. 6, pp. 806-815, vol. 27.

W21. D. M. Suiter and S. B. Leder, "Clinical utility of the 3-ounce water swallow test," Dysphagia, vol. 23, No. 3, pp. 244-250, Sep. 2008.

W28. Dyer JC, Leslie P, Drinnan MJ: Objective computer-based assessment of valleculae residue: Is it useful? Dysphagia. 2008;23:7-15.

D55. J. Lee, C. M. Steele, and T. Chau, "Time and time-frequency characterization of dual-axis swallowing accelerometry signals," Physiological Measurement, vol. 29, No. 9, pp. 1105-1120, Sep. 2008.

W33. Kim, et al., "Maximum Hyoid Displacement in Normal Swallowing," Dysphagia, Sep. 2008, No. 3, pp. 274-279, vol. 23.

D57. Lindsay, et al., Canadian best practice recommendations for stroke care, Canadian Medical Association Journal, Dec. 2008, No. 12, pp. El-E93, vol. 179.

D58. Martino, et al., "Screening for Dysphagia in Stroke Survivors: A Before and After Implementation Trial of Evidence-Based Care," Dysphagia, Dec. 2008, No. 4, pp. 429-430, vol. 23.

D59. Moriniere, et al., "Origin of the Sound Componenets during Pharngeal Sallowing in Normal Subjects," Dysphagia, Sep. 2008, No. 3, pp. 267-273, val. 23.

W10. N.-J. Paik, S. J. Kim, H. J. Lee, J. Y. Jeon, J.-Y. Lim, and T. R. Han, "Movement of the hyoid bone and the epiglottis during swallowing in patients with dysphagia from different etiologies," Journal of Electromyography and Kinesiology, vol. 18, No. 2, pp. 329-335, Apr. 2008.

D60. Bours, et al., "Bedside Screening Tests vs. Videofluoroscopy or Fibreoptic Endoscopic Evaluation of Swallowing to Detect Dysphagia in Patients with Neurological Disorders: Systematic Review," Journal of 2009, No. 3, pp. 477-493, vol. 65. Advanced Nursing, Mar. D.

D61. Bravata, et al., "Comparison of Two Approaches to Screen for Dysphagia Among Acute Ischemic Stroke Patients: Nursing Admission Screening Tool Versus National Institutes of Health Stroke Scale," Journal of Research and Development, 2009, No. 9, pp. 1127-1134, vol. 46. Rehabilitation D.

W31. Coyle, et al., "Oropharyngeal Dysphagia Assessment and Treatment Efficacy: Setting the Record Straight," Journal of the American Medical Directors Association, Jan. 2009, No. 1, pp. 62-66, vol. 10.

D64. E. Sejdic, C. M. Steele, and T. Chau, "Segmentation of dual-axis swallowing accelerometry signals in healthy subjects with analysis of anthropometric effects on duration of swallowing activities," IEEE Transactions on Biomedical Engineering, vol. 56, No. 4, pp. 1090-1097, Apr. 2009.

\* cited by examiner

TABLE 1

Improvements in SNR (dB) upon application of the considered approaches to three types of swallowing signals.

| Type | Donoho A-P | Donoho S-I | MNDL A-P | MNDL S-I | SURE A-P | SURE S-I | Proposed A-P | Proposed S-I |
|---|---|---|---|---|---|---|---|---|
| Dry | 5.8 ± 1.8 | 4.1 ± 2.7 | 5.4 ± 0.3 | 5.1 ± 0.5 | 5.8 ± 4.2 | 6.5 ± 6.1 | 9.3 ± 1.8 | 7.8 ± 1.9 |
| Wet | 5.4 ± 1.3 | 3.4 ± 2.0 | 5.4 ± 0.3 | 5.1 ± 0.7 | 6.9 ± 4.3 | 6.3 ± 3.9 | 9.0 ± 1.6 | 7.3 ± 1.6 |
| WCT | 2.9 ± 1.7 | 2.2 ± 1.9 | 5.2 ± 0.3 | 5.0 ± 0.4 | 7.1 ± 3.9 | 5.1 ± 5.5 | 7.5 ± 1.2 | 7.0 ± 1.4 |
| Overall | 4.8 ± 2.1 | 3.3 ± 2.4 | 5.3 ± 0.3 | 5.0 ± 0.5 | 6.6 ± 4.2 | 6.0 ± 5.4 | 8.6 ± 1.8 | 7.3 ± 1.7 |

FIGURE 2

PROCEDURE FOR DENOISING DUAL-AXIS SWALLOWING ACCELEROMETRY SIGNALS

CROSS REFERENCE TO RELATED APPLICATIONS

This application claims the benefit of U.S. Provisional Patent Application No. 61/218,976 filed on Jun. 21, 2009

FIELD OF INVENTION

This invention relates in general to the field of dual-axis swallowing accelerometry signal analysis and more specifically to a method for denoising such signals.

BACKGROUND OF THE INVENTION

Swallowing accelerometry is a potentially informative adjunct to bedside screening for dysphagia. These measurements are minimally invasive, requiring only the superficial attachment of a sensor anterior to the thyroid notch. Even though single-axis accelerometers were traditionally used for swallowing accelerometry, recent studies have shown that dual-axis accelerometers can capture more of the clinically relevant information. Nevertheless, such measurements are inherently very noisy due to various physiological and motion artifacts. Denoising of dual-axis swallowing accelerometry signals is therefore essential for the development of a robust medical device based on these signals.

Estimation of unknown signals in white Gaussian noise has been dealt with by others. Wavelet denoising has previously been proposed as a valuable option. Wavelet denoising removes the additive white Gaussian noise from a signal by zeroing the wavelet coefficients with small absolute value. The suggested optimal threshold is equal to $\sigma_\epsilon \sqrt{2 \log N}$ where $\sigma_\epsilon^2$ is the variance of the additive noise and N is the length of the signal. This approach requires the knowledge of the noise variance, which can be estimated from the wavelet coefficients at the finest scale. However, wavelet denoising with the suggested optimal threshold does not necessarily produce the optimal results for signals that are not smooth. i.e., signals with noiseless coefficients being of very small amplitude for a large number of basis functions. Recent attempts to overcome this shortcoming have yielded methods that can suffer from high computational complexities for very long signals, and do not necessarily reach the optimal results.

It is an object of this invention to: (1) reduce high computational complexity; and, (2) reduce reconstruction error associated with denoising swallowing accelerometry signals.

SUMMARY OF THE INVENTION

This invention teaches a method for denoising of long duration dual-axis swallowing accelerometry signals using a computationally efficient algorithm. The algorithm achieves low computational complexity by performing a search for the optimal threshold in a reduced wavelet subspace. To find this reduced subspace, the proposed scheme uses the minimum value of the estimated reconstruction error. By finding this value, the proposed approach also achieves a smaller reconstruction error than previous approaches such as MNDL. SURE-based and Donoho's approaches. This finding has been confirmed for both, synthetic test signals and dual-axis swallowing accelerometry signals.

BRIEF DESCRIPTION OF THE DRAWINGS

In the drawings, embodiments of the invention are illustrated by way of example. It is to be expressly understood that the description and drawings are only for the purpose of illustration and as an aid to understanding, and are not intended as a definition of the limits of the invention.

FIG. 2 is a table, identified as Table 1, of SNRs (dB) between the Donoho approach and the method of the present invention.

DETAILED DESCRIPTION

Methodology of the Invention

Figure 1:
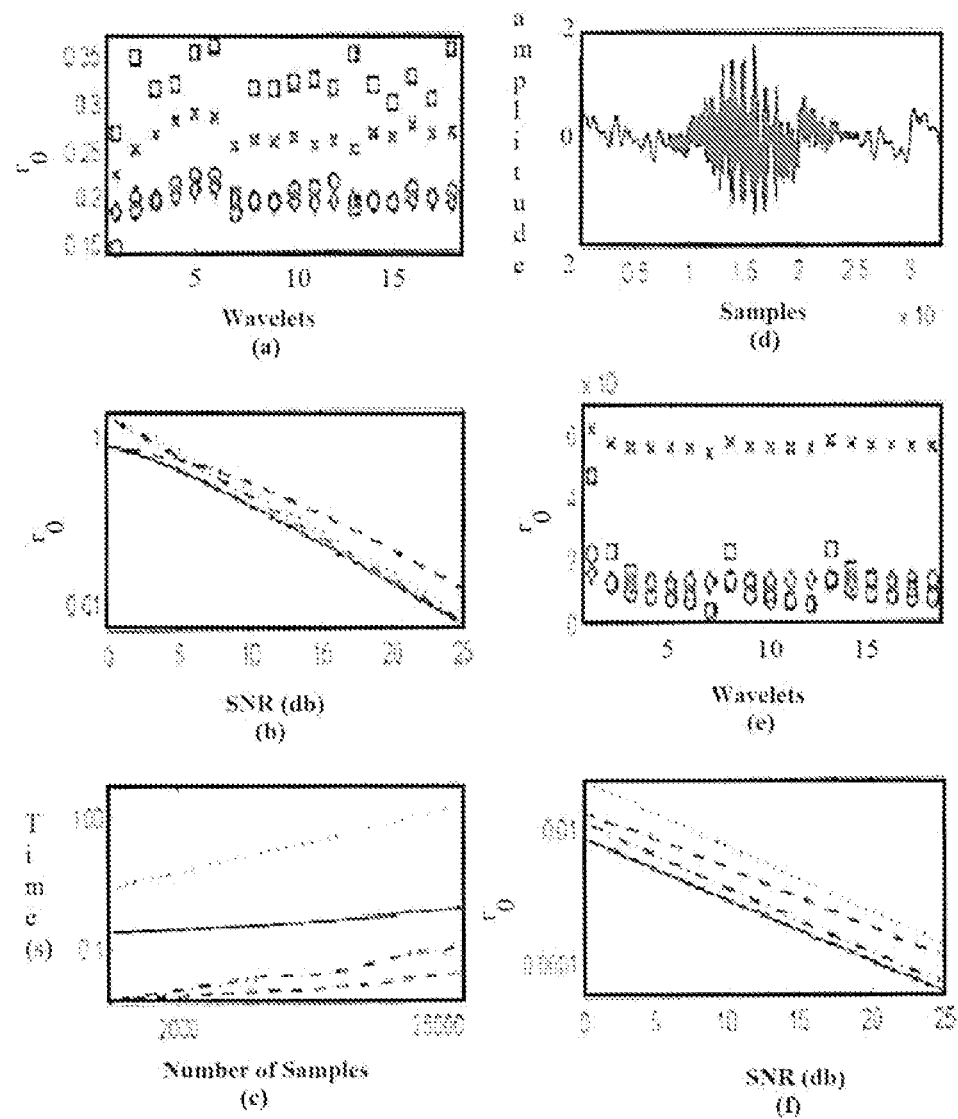
FIG. 1 is a series of six graphs (a) to (f) comparing the denoising approach of the method of the present invention to the MDL-based and Donoho approaches.

Consider N noisy discrete-time observations:

$$x(n) = f(n) + \epsilon(n) \quad (1)$$

where $n=0, \ldots, N-1$, $f(n)$ is a sampled version of a noiseless continuous signal, and $\epsilon(n)$ is the additive white Gaussian noise drawn from $N(0, \sigma_\epsilon^2)$ Assume that $f(n)$ can be expanded using basis functions, $b_k(n)$, on the observation space, $B_N$:

$$f(n) = \Sigma_{k=1}^N c_k b_k(n) \quad (2)$$

where $$c_k = \langle b_k(n), f(n) \rangle \quad (3)$$

and $(p,q)$ denotes the inner product of vectors p and q. However, given the noisy observations, the coefficients, $c_k$, can only be approximated as follows:

$$\hat{c}_k = \langle b_k(n), x(n) \rangle = c_k + \langle b_k(n), \epsilon(n) \rangle \quad (4)$$

Denoising and Reconstruction Error

If $f(n)$ can be described with M nonzero coefficients, where $M \ll N$, then many estimated coefficients, $\hat{c}_k$, represent samples of a zero mean Gaussian random variable with variance $\sigma_\epsilon^2$. A classical approach known as wavelet denoising diminishes the effects of noise by first expanding the noisy signal in terms of orthonormal bases of compactly supported wavelets. The estimated coefficients below some threshold, $\tau$, are disregarded either by hard or soft thresholding. The value of $\tau$ is always chosen based on an attempt to minimize the so-called reconstruction error, $r_e$:

$$r_e = \frac{1}{N} \| f(n) - \hat{f}(n) \|^2 \quad (5)$$

where $\|\cdot\|$ denotes the Euclidean norm and $\hat{f}(ii)$ represents the estimated noiseless signal. $r_e$ is a sample of random variable $R_e$ that has the following expected value:

$$E\{R_e\} = \frac{m}{N}\sigma^2 + \frac{1}{N}\|\Delta m\|^2 \quad (6)$$

where m represents the number of coefficients describing $f(n)$ in some subspace of $B_N$ and $\Delta m$ is a vector of length N-m, representing the coefficients of bases that are not selected to describe the unknown signal. In reality, $r_e$ is not available and only the number of coefficients not disregarded by the thresholding operation, $\hat{m}$, is known. In a recent contribution, probabilistic upper and lower bounds for $r_e$ were derived based on the available data error:

$$d_e = \frac{1}{N}\|x(n) - \hat{f}(n)\|^2 \quad (7)$$

Therefore, it, has been shown that the upper bound for $r_e$ is equal to $$r_{eub}(\hat{m}(\tau), \sigma^2, \alpha, \beta) = \frac{\sigma_\varepsilon^2 \sqrt{2\hat{m}(\tau)}}{N}\left(\sqrt{2\hat{m}(\tau)} + \beta\right) + d_e - \sigma_\varepsilon^2 + \frac{2\alpha\sigma_\varepsilon}{\sqrt{N}}\left(\frac{\alpha\sigma_\varepsilon}{\sqrt{N}} + \sqrt{\frac{\alpha^2\sigma_\varepsilon^2}{N} + d_e - \left(1 - \frac{\hat{m}(\tau)}{N}\right)\frac{\sigma_\varepsilon^2}{2}}\right), \quad (8)$$

where $\alpha$ and $\beta$ represent the parameters for validation probability ($P_v = Q(\alpha)$) and confidence probability ($P_c = Q(\beta)$), with $Q(\cdot)$ for an argument $\lambda$ being, defined as $$Q(\lambda) = \int_{-\lambda}^{+\lambda}\left(\frac{1}{\sqrt{2\pi}}\right)e^{-x^2/2}dx.$$

In addition, $\hat{m}(\tau)$ denotes the number of bases whose expansion coefficients are greater than $\tau$ in some subspace of $B_N$.

It should be note that for some values of $\hat{m}$ the reconstruction error given by eqn. (5) and its upper bound given by eqn. (8) achieve a minimum due to the bias-to-variance trade-off. The principle of MDL has been borrowed from coding theory to find such a minimum value. Also, it has been demonstrated that, smaller reconstruction errors can be achieved with MDL-derived thresholds.

Algorithm for Determining Optimal Threshold

The MNDL-based approach can be computationally expensive for very long data sets since the bases are incrementally added to the subspace describing the unknown signal. Considering the length of acquired dual-axis accelerometry signals ($>>10^5$ points}, an attempt should be made to minimize the search space, while choosing a threshold that minimizes the reconstruction error. In some cases the MNDL-based approach can yield higher reconstruction errors than Donoho's approach.

In light of the computational and reconstruction limitations or the MNDL-based approach, a new denoising strategy is proposed here. The goal of this new approach is twofold. First, it should be computationally efficient. Second, it should attain a minimum reconstruction error. Minimization of the search space can be achieved by exploiting the fact that the optimal threshold is usually larger than the actual threshold which minimizes the reconstruction error. The algorithm for determining the optimal threshold is defined through the following steps:

1. Estimate the variance of the noise $\varepsilon$ from the median, $MED_x$, of $N/2$ wavelet coefficients at the finest scale:

$$\hat{\sigma}_\varepsilon = \frac{MED_x}{0.6745} \quad (9)$$

2. Based on the estimated noise variance, and for each $\tau$ selected from a set $0 < \tau \leq \hat{\sigma}_\varepsilon\sqrt{2\log(N)}$, evaluate the upper bound given by equation (8). Use the soft thresholding procedure to compute the data error required for the evaluation of the upper bound.

3. Determine the optimal threshold for wavelet denoising as:

$$\tau_{opt} = \operatorname*{argmin}_{\tau} r_{eub}(\hat{m}(\tau), \sigma^2, \alpha, \beta) \quad (10)$$

4. Denoise a recording using the optimal value of threshold, $\tau_{opt}$, and the soft thresholding procedure.

The above procedure is repeated independently for signals acquired from each axis of a dual-axis accelerometer. Unlike the MNDL-based approach, soft thresholding is applied in the above steps, since it yields an estimated signal as smooth as the original signal with high probability. Hard thresholding can produce abrupt artifacts in the recovering signal leading to a higher reconstruction signal.

Numerical Analysis

The results of a two-step numerical analysis are presented in this section. First, the performance of the proposed algorithm is examined using two test signals. The goal of this analysis is to compare the performance of the proposed scheme against that of other well-established techniques under well-controlled conditions. In the second step, the proposed denoising algorithm is applied to the acquired dual-axis swallowing accelerometry signals. The goal is to understand the benefits of the proposed approach in the context of a real biomedical application.

Performance Analysis Using Synthetic Test Signals

Referring to FIG. 1, the first test signal is the so-called Blocks signal, which is a standard signal used in the analysis of various denoising schemes. Assuming that the length of the signal is N=1024 points, the reconstruction error is evaluated for four methods: the proposed method, and the MNDL-based method and a new SURE-based approach. The first test is to numerically examine which of the four schemes provides the lowest reconstruction error for 18 mother wavelets (Haar wavelet, Daubechies wavelets with the number of vanishing moments varying between two and six, Meyer wavelet, Coiflet wavelets with the order varying, between one and five, and Symlet wavelets with the order varying between two and seven). The signal is contaminated with zero-mean additive white Gaussian noise, and SNR=10 dB. For each mother wavelet, 1000 realizations are used. $\alpha=10$ and $\beta=40$ are used for both the MNDL-based approach and the proposed method. The reconstruction errors for the proposed method (circles), the MNDL-based denoising (x'S), the SURE-based approach (diamonds) and Donoho's approach (squares) are shown in FIG. 1(a). Amongst the 18 wavelet functions, considered, the Haar wavelet (the wavelet indexed as 1 on the x-axis of FIG. 1(a)) provides the smallest reconstruction error, since, the structure of the wavelet closely resembles the structure of the signal.

The next task is to examine the reconstruction error under various SNR values with the Haar wavelet. One thousand realizations are used for each SNR value yielding the results depicted in FIG. 1(b). From the graph, it is clear that the proposed method (solid line) provides the smallest error for various SNR levels with the MNDL-based (dotted line) and SURE-based (dashdotted line) methods also providing a small error. Donoho's approach (dashed line) consistently yields the highest reconstruction error. Despite the small reconstruction error over different SNL levels, the MNDL-based method suffers from high computational complexity. To further understand the computational bottlenecks, the SNR value is kept constant at 10 dB, but the length of the Blocks signal is varied between $N=2^{10}$ and $N=2^{15}$ points. The durations required to execute the specific algorithms are tracked using built-in MATLAB functions. The time to complete the denoising task, averaged over ten realizations of the Block signal at each signal length is reported in FIG. 1(c). As expected, as N increases, there is an obvious upward trend for all for algorithms. Donoho's approach (dashed line) is the least computationally expensive. However, for the MNDL-based approach (dotted line) the time required to complete the task increases significantly with signal length. For example, the average duration required for the MNDL-based approach to denoise a signal with length of $N=2^{15}$ points is 157 seconds. On the other hand, the time required by the proposed algorithm (solid line) to denoise the same signal is 0.74 seconds. In fact, computation time of the proposed method increases logarithmically with signal length (the duration is approximately equal to $\log_{10}(N^{0.35})$).

To more closely mimic a real swallowing scenario, the test signal shown in FIG. 1(d), is used in the analysis. The signal is defined as:

$$f(n) = \begin{cases} f_o(n) + 0.6\cos(210\pi nT) & 8100 \le n \le 16430 \\ f_o(n) + 0.5\cos(140\pi nT) & 11400 \le n \le 18330 \\ f_o(n) + 0.2\cos(120\pi nT) & 13200 \le n \le 25230 \\ f_o(n) + 0.4\cos(160\pi nT) & 12250 \le n \le 23400 \\ f(n)w(n) & 8100 \le n \le 25230 \end{cases} \quad (11)$$

where w(n) is Gaussian window with standard deviation $\sigma_g=1.9$ and $$f_0(n)=0.1\sin(8\pi nT)+0.2\sin(2\pi nT)+0.15\sin(20\pi nT)+ \\ 0.15\sin(6\pi nT)+0.12\sin(14\pi nT)+0.1\sin(4\pi nT) \quad (12)$$

with $0 \le n \le N-1$, $N=35000$ and $T=10^{-4}$ seconds. The duration of the signal is based on previously reported swallow durations. It should be mentioned that this signal only mimics a realistic signal, and does not represent a model of a swallow. The same group of wavelets as in the Blocks signal analysis are used to examine the reconstruction error. It is assumed again that the signal is contaminated with additive zero-mean Gaussian noise and SNR=0.10 dB. For this particular signal, the Meyer wavelet (indexed by number 7 in FIG. 1(e)) achieved the smallest reconstruction error since the structure of the wavelet resembles the structure of the signal. It should be pointed out that the MNDL-based method consistently provides the highest error for all considered wavelets. Given that the method is sensitive to the choice of $\alpha$ and $\beta$ we varied the two parameters to further examine the obtained error. The MNDL method still maintained the highest reconstruction error for this particular signal. The main reason for these results is the hard-thresholding procedure used in this method. Consequently, the better results are indeed expected with an approach implementing a soft-thresholding procedure. As the next step, the reconstruction error is evaluated using the Meyer wavelet for various SNR values for all four approaches. From the results shown in FIG. 1 (f), it is obvious that the proposed method (solid line) achieves a significantly smaller reconstruction error than the other three methods.

Denoising Dual-Axis Swallowing Accelerometry Signals
Experimental Protocol

Figure 3:
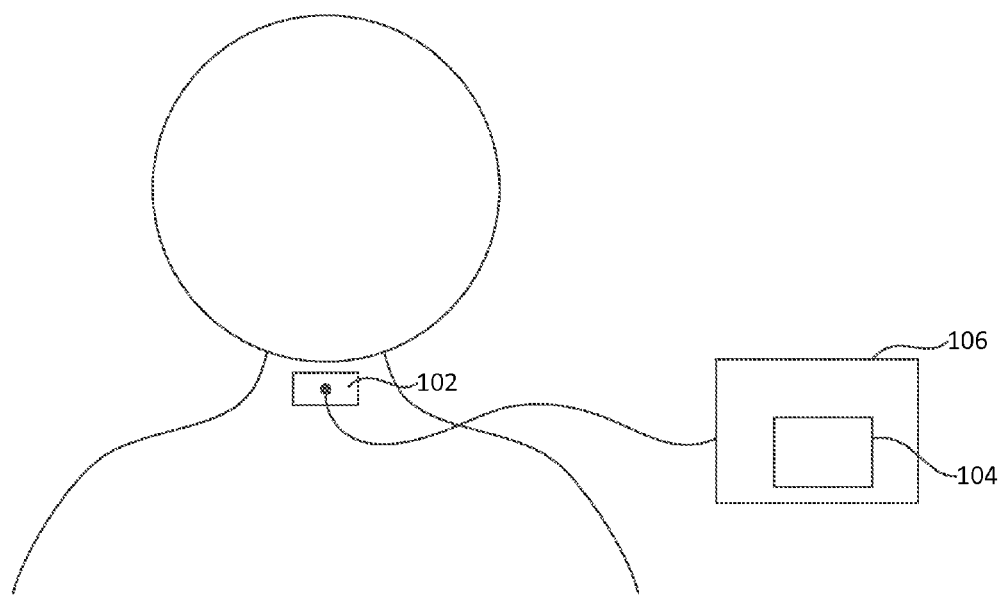
FIG. 3 is a schematic view of a system for acquiring dual-axis swallowing accelerometry signals to be denoised by the denoising method of the present invention.

During a three month period, four hundred and eight participants (aged 18-65) were recruited at a public science centre. All participants provided written consent. The study protocol was approved by the research ethics boards of the Toronto Rehabilitation Institute and Bloorview Kids Rehab, both located in Toronto, Ontario, Canada. As seen in FIG. 3, a dual-axis accelerometer 102 (ADXL322, Analog Devices) was attached to the participant's neck (anterior to the cricoid cartilage) using double-sided tape, and an output signal of the accelerometer 102 was communicated to a signal processor 104 of a computer 106. The axes of acceleration were aligned to the anterior-posterior (A-P) and superior-inferior (S-I) directions. Data were band-pass filtered in hardware with a pass band of 0.1-3000 Hz and sampled at 10 kHz using a custom LabVIEW program running on a laptop computer.

With the accelerometer attached, each participant was cued to perform 5 saliva swallows (denoted as dry in Table 1). After each swallow, there was a brief rest to allow for saliva production. Subsequently, the participant completed 5 water swallows (denoted as wet in Table 1) by cup with their chin in the natural position (i.e., perpendicular to the floor) and water swallows in the chin-tucked position (denoted as WTC in Table 1). The entire data collection session lasted 15 minutes per participant.

Results of Denoising

The acquired dual-axis swallowing accelerometry signals were denoised using Donoho's approach, the MNDL-based approach, the SURE-based approach and the proposed approach. In particular, a 10-level discrete wavelet transform using the Meyer wavelet with soft thresholding was implemented. Before denoising, the signals were pre-processed using inverse filters to annul effects of the data collection system on the acquired data. In order to compare the performance of the aforementioned denoising schemes, SNR values were evaluated before and after denoising using the following formula:

$$SNR = 10\log_{10}\left(\frac{E_f}{E_{\hat{\epsilon}}}\right) \quad (13)$$

where $E_f$ represents the approximate energy of the noise-free signal, and $E_{\hat{\epsilon}}$ represents an approximate variance of the white Gaussian noise. The approximate energy is calculated as $E_f = \hat{\sigma}_x^2 = \hat{\sigma}_\epsilon^2$, where $\hat{\sigma}_x^2$ is the variance of the observed signal, and $\hat{\sigma}_\epsilon^2$ represents the variance of the noise calculated by (9). Similarly, $E_{\hat{\epsilon}} = \hat{\sigma}_x^2$ for the noisy signals, and for the denoised signals $E_{\hat{\epsilon}} = r_{eub}(\hat{m}(\tau), \hat{\sigma}_\epsilon^2, \alpha, \beta)$ for the threshold estimated by (10).

Using the SNR metric given by (13), the results of the analysis are summarized in Table 1. Donoho's approach provides the least amount of improvement in SNR as expected, followed by the MNDL-based approach. The SURE-based approach achieves greater improvement in the SNR values in comparison to the other two aforementioned approaches. Nevertheless, as demonstrated by the results in Table 1, the SURE approach exhibits strong variations in performance. The proposed approach provides the greatest improvement in SNR values. On average, the greatest gain in SNR is over Donoho's approach (3.8 dB and 4.0 dB in the A-P and S-I directions, respectively), while smaller improvements were obtained over the SURE-based approach (2.0 dB and 1.3 dB in the A-P and S-I directions, respectively). Nevertheless, the proposed approach still provides a statistically significant improvement over SURE-based approach in denoising the dual-axis swallowing accelerometry signals (Wilcoxon rank-sum test, $p \ll 10^{-10}$ for both directions). This improvement was achieved regardless of whether or not the different swallowing types were considered individually or as a group. As a last remark, it should be noted that these SNR values were estimated using eqn. (13), which from our experience with swallowing signals, provides a conservative approximation. In reality, we expect the gains in SNR to be even greater.

CONCLUSION

A denoising algorithm is proposed for dual-axis swallowing accelerometry signals, which have potential utility in the non-invasive diagnosis of swallowing difficulties. This algorithm searches for the optimal threshold value in order to achieve the minimum reconstruction error for a signal. To avoid the high computational complexity associated with competing algorithms, the proposed scheme conducts the threshold search in a reduced wavelet subspace. Numerical analysis showed that the algorithm achieves a smaller reconstruction error than Donoho, MNDL- and SURE-based approaches. Furthermore, the computational complexity of the proposed algorithm increases logarithmically with signal length. The application of the proposed algorithm to dual-axis swallowing accelerometry signals demonstrated statistically significant improvements in SNR over the other three considered methods.

What is claimed is:

1. A computer executed procedure for denoising swallowing accelerometry signals, the procedure executed by a processor coupled to memory of the computer on a signal output from an accelerometer attached to a person's neck during swallowing, the procedure comprising:
defining a set of N discrete time observations from said signal to have a noiseless component f(n) and a noise component $\epsilon(n)$;
estimating a set of wavelet coefficients $c_k$ for said noiseless component f(n);
estimating a variance $\hat{\sigma}_\epsilon$ of the noise component $\epsilon(n)$ from a median $MED_x$ of a finest scale subset of said wavelet coefficients;
defining a set of wavelet coefficient threshold values $\tau$ within a range thereof defined as function of said estimated variance, wherein the wavelet coefficient threshold values $\tau$ are each selected from a set $0<\tau\leq\hat{\sigma}_\epsilon\sqrt{(2\log(N))}$;
for each of said threshold values $\tau$, calculating an upper bound for a reconstruction error $r_e$;
selecting an optimal threshold value $\tau_{opt}$ from said set of threshold values that minimizes said upper bound; and
denoising the signal by suppressing those of said wavelet coefficients below said optimal threshold value,
wherein the upper bound is determined by $$r_{eub}(\hat{m}(\tau), \sigma^2, \alpha, \beta) = \frac{\sigma_\varepsilon^2 \sqrt{2\hat{m}(\tau)}}{N}\left(\sqrt{2\hat{m}(\tau)} + \beta\right) + d_e - \sigma_\varepsilon^2 + \frac{2\alpha\sigma_\varepsilon}{\sqrt{N}}\left[\frac{\alpha\sigma_\varepsilon}{\sqrt{N}} + \sqrt{\frac{\alpha^2\sigma_\varepsilon^2}{\sqrt{N}} + d_e - \left[1 - \frac{\hat{m}(\tau)}{N}\right]\frac{\sigma_\varepsilon^2}{2}}\right].$$

2. The computer executed procedure of claim 1, wherein said suppressing comprises suppressing via one of a hard and a soft thresholding process.

3. The computer executed procedure of claim 2, wherein said suppressing comprises suppressing via a soft thresholding process.

4. The computer executed procedure of claim 1, wherein the signal is output from a dual-axis accelerometer.

5. The computer executed procedure of claim 4, wherein the procedure is executed independently for signals acquired from each axis of the dual-axis accelerometer.

6. The computer executed procedure of claim 1, wherein said finest scale subset consists of N/2 finest scale wavelet coefficients.

7. The computer executed procedure of claim 6, wherein the variance $\hat{\sigma}_\epsilon$ of the noise component $\epsilon(n)$ is estimated from the median $MED_x$ of the finest scale subset consisting of N/2 finest scale wavelet coefficients by dividing $MED_x$ by 0.6745.

* * * * *